United States Patent [19]

Kreitman

[11] Patent Number: 4,766,892

[45] Date of Patent: Aug. 30, 1988

[54] LIMB RESTRAINT

[76] Inventor: Gary Kreitman, 8700 N. Kendall Dr., Miami, Fla. 33176

[21] Appl. No.: 756,794

[22] Filed: Jul. 19, 1985

Related U.S. Application Data

[63] Continuation of Ser. No. 172,401, Jul. 25, 1980, abandoned.

[51] Int. Cl.[4] .............................................. A61F 13/00

[52] U.S. Cl. ..................................... 128/134; 269/328

[58] Field of Search ....... 128/134, 133, 1 R, DIG. 20; 269/328

[56] References Cited

U.S. PATENT DOCUMENTS

| | | | |
|---|---|---|---|
| 2,266,231 | 12/1941 | Mazzeo et al. | 269/328 X |
| 2,535,559 | 12/1950 | Wolf | 269/328 |
| 3,218,103 | 11/1965 | Boyce | 128/134 |
| 3,244,415 | 12/1965 | Gottfried | 128/DIG. 20 X |
| 3,825,008 | 7/1974 | Shook . | |
| 4,122,587 | 10/1978 | Weiss et al. | 269/328 X |
| 4,181,297 | 1/1980 | Nichols | 269/328 |
| 4,232,681 | 11/1980 | Tulaszewski | 128/133 X |
| 4,299,213 | 11/1981 | Violet | 128/133 |
| 4,526,165 | 7/1985 | Mielnik | 128/133 |
| 4,549,540 | 10/1985 | Caspari et al. | 128/133 |

FOREIGN PATENT DOCUMENTS

| | | | |
|---|---|---|---|
| 3113685 | 10/1982 | Fed. Rep. of Germany | 128/133 |
| 329692 | 2/1903 | France | 128/134 |
| 1558746 | 1/1969 | France | 269/328 |

*Primary Examiner*—Robert A. Hafer
*Assistant Examiner*—Danton D. DeMille
*Attorney, Agent, or Firm*—Natter & Natter

[57] ABSTRACT

A limb restraint adapted for orthopedic examinations and operating procedures provides a firm support for a portion of a patient's limb while the limb or a joint is manipulated or stressed. The restraint includes a rigid frame which defines a partially enclosed area within which the patient's limb is inserted. The enclosed area of the frame accommodates a blood pressure type air bag cuff or tourniquet which is secured to the frame by a fastener. Restraintive force is applied to the limb and monitored by pressurizing the air bag to a controlled level. In one embodiment, the partially enclosed area is shaped as an inverted "U" and with the operating table providing the bottom closure. In a further embodiment, the frame includes a horizontal way which extends along the operating table and terminates at an upward laterally curve jaw. An adjustable medially curved jaw is positionable along the way. After the adjustable jaw has been positioned, the air bag is pressurized to restrain the limb.

15 Claims, 2 Drawing Sheets

FIG. 5
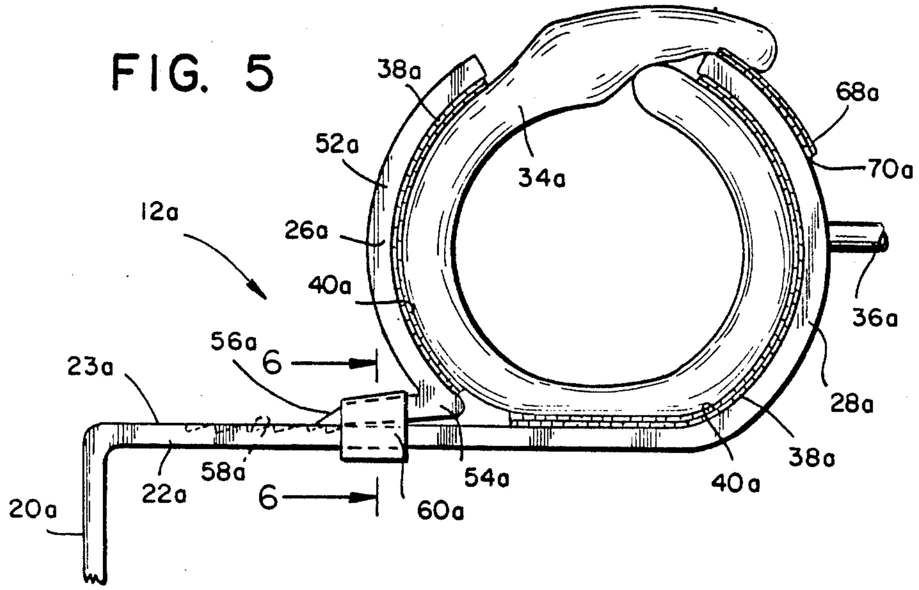
FIG. 6
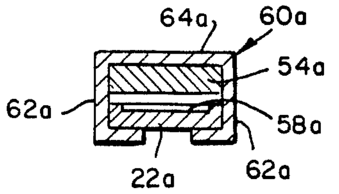
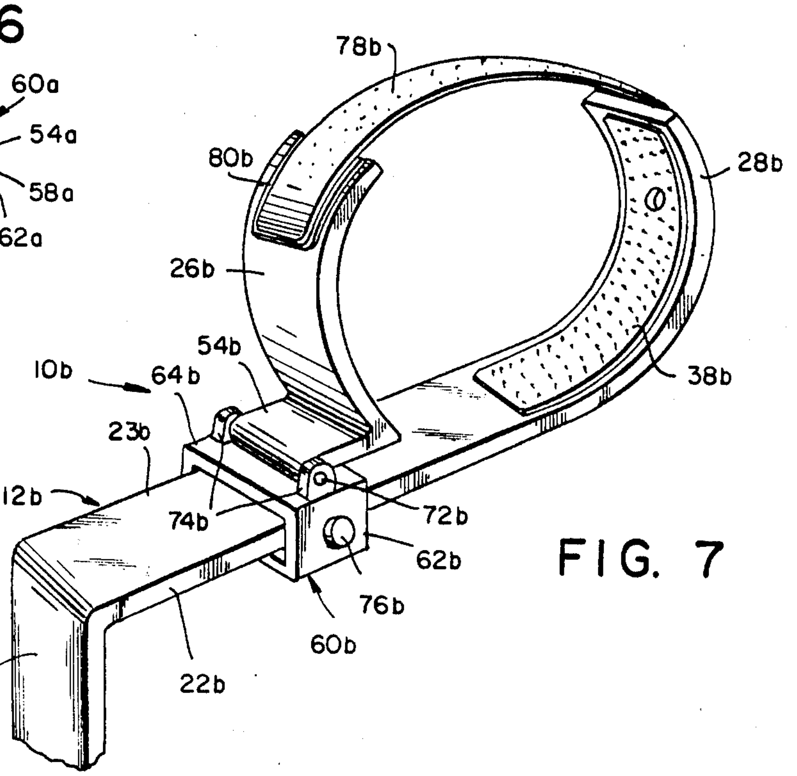
FIG. 7

LIMB RESTRAINT

BACKGROUND OF THE INVENTION

1. Field of the Invention

This invention relates generally to positioning devices for use in orthopedic examinations and/or operating procedures and more specifically to a limb restraint.

2. Brief Description of the Prior Art

During orthopedic examinations and/or operating procedures, physicians including orthopedic surgeons, radiologists and others were required to manipulate limbs to obtain desired spacial relationships between bones and/or joint components. Typically, when a fracture was to be set, one portion of the limb was held fast while the other portion was manipulated for alignment of the fractured segments. This procedure was often difficult unless the physician was assisted so that he could manipulate the distal or free end of the limb while the remaining area of the limb was held.

In instances wherein more than one person was employed during an operating procedure which required the application of various forces to a limb, control of the limb movement was difficult since the precise force applied by an assistant was not under the direct control of the operating physician.

In conjunction with the diagnosis, examination and treatment of knee injuries, the application of a restraintive force at the patient's thigh has been required. Such restraintive force permitted manipulation of the tibia by an examining or operating physician so that varus and valgus stresses could be applied to the knee joint. The applied varus and valgus stresses accessed areas of the joint to arthroscopic examination as well as surgical procedures.

A typical example of restraintive devices for use in conjunction with knee joint diagnostic procedures, e.g. taking arthrograms, was illustrated in U.S. Pat. No. 4,181,297. The device disclosed therein included a suction mount for a smooth x-ray table and a pair of movable curved jaws. The jaws were positionable along a support plate and each engaged one of a plurality of notches in the plate. Because the adjustment mechanism for the jaws only provided fixed increment adjustments, precise control of the restraintive pressure applied by the jaws to the patient's thigh was not attainable. Furthermore, the jaw surfaces which abutted the patient's thigh were not protected and presented a possible source of injury. In addition, this device was not employable during operating procedures since the suction mount adhered only to the smooth flat x-ray table.

In the field of sports medicine, arthroscopic knee joint examinations and surgical procedures have accentuated the need for suitable limb restraints. One device which attempted to meet this need provided a metal restraint with movable C shaped jaws. A vise screw mechanism was utilized to position the jaws for adjustment of the restraintive force applied against the patient's thigh. Although the jaws were padded, difficulty was encountered in effectively using this device. A significant problem which has been encountered was that the physician was not able to monitor the restraintive force which was applied against the thigh. When excessive force was applied through the vise screw jaw mechanism, the device acted as a tourniquet. As such it presented hazards, interfering with the operation of the conventional tourniquet usually employed during surgical procedures and, in addition, damaging thigh tissue.

SUMMARY OF THE INVENTION

In compendium, the present invention comprises a limb restraint for therapeutic, diagnostic and surgical procedures which engages a patient's limb with a circumscribing air bag for the application of a precisely controlled and monitored restraintive force. The air bag is secured and referenced to a rigid frame which, in turn, is mounted to an operating and/or examining table.

The frame includes a pair of spaced side panels joined by a top plate and is adapted for placement over a patient's limb with the limb situated between the side panels, the top plate and the table. The air bag is secured to the interior surfaces of the frame, i.e. side panels and top plate, by a hook and loop fastener. In alternate embodiments, the frame comprises a horizontal way which extends transversely across the operating and/or examining table. A curved jaw extends from the free end of the way while a second jaw engages a carriage which is adjustably positioned on the way. The patient's limb is placed over the way, the air bag is positioned around the limb and the adjustable jaw positioned. A hook and loop type fastener engagement between the periphery of the air bag and the interior jaw faces secures the air bag to the frame.

In one alternate embodiment, the adjustable jaw includes a tang which engages one of a plurality of stop notches formed in the way. A further alternate embodiment includes a hinge which pivotally mounts the adjustable jaw to the carriage, and a fastener strip is employed between the free ends of each jaw.

From the above summary, it will be appreciated that it is an object of the present invention to provide a limb restraint of the general character described which is not subject to the disadvantages of the prior art as aforementioned.

A further object of the present invention is to provide a limb restraint of the general character described which is simple to operate yet permits precise control and monitoring of restraintive forces.

A further object of the present invention is to provide a limb restraint of the general character described which is relatively low in cost and suitable for economical mass fabrication techniques.

A further object of the present invention is to provide a limb restraint of the general character described which permits even distribution of restraintive forces around a patient's limb.

Another object of the present invention is to provide a limb restraint of the general character described which simplifies the routine application of effective restraintive force to a patient's limb without injury to the tissue of the restrained area.

Other objects of the present invention in part will be obvious and in part will be pointed out hereinafter.

With these ends in view, the invention finds embodiment in the various combinations of elements, arrangements of parts and series of steps by which the said objects and certain other objects are attained, all as more fully described with reference to the accompanying drawings and the scope of which is more particularly pointed out and indicated in the appended claims.

BRIEF DESCRIPTION OF THE DRAWINGS

In the accompanying drawings in which are shown some of the various possible exemplary embodiments of the invention:

FIG. 5 is an elevational view of the limb restraint in accordance with the embodiment of FIG. 4, the same being viewed substantially along the plane 5—5 of FIG. 4 and showing an air bag in position;

FIG. 6 is a sectional view through a carriage which fixes the position of the movable jaw, the same being taken substantially along the line 6—6 of FIG. 5; and FIG. 7 is a fragmentary perspective illustration of a still further embodiment of the invention also employing an adjustably positioned jaw with the jaw pivotally mounted to a carriage and with the air bag being removed to better illustrate the frame.

DESCRIPTION OF THE PREFERRED EMBODIMENTS

Figure 1:
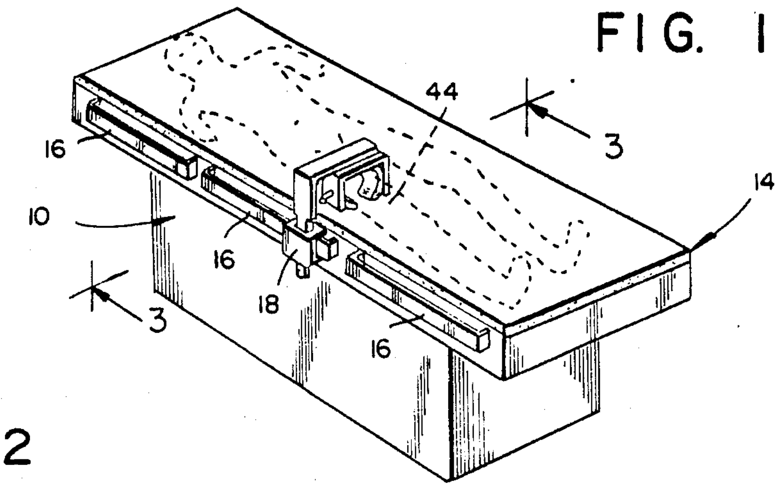
FIG. 1 is a perspective illustration of a limb restraint constructed in accordance with and embodying the present invention and showing the limb restraint, including a frame and an air bag, in use and attached to an operating table.
Figure 2:
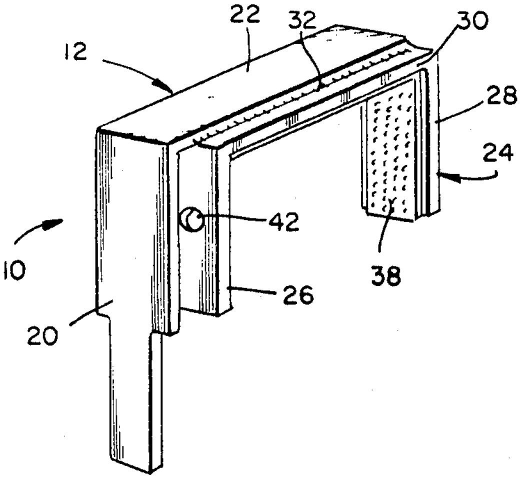
FIG. 2 is a perspective illustration of the limb restraint frame with the limb engaging air bag removed to better illustrate various components.

Referring now in detail to the drawings, the reference numeral 10 denotes generally a limb restraint constructed in accordance with and embodying the invention. The limb restraint 10 is adapted to provide a firm support for a portion of a patient's limb during diagnostic and/or surgical manipulation of the limb.

The restraint 10 includes a rigid frame 12 which is adapted to be secured to an operating or examining table 14. The table 14 includes a plurality of support rails 16 to which a collar mount 18 is attached. The collar mount 18 may be adjustably positioned along a support rail 16 and fixed at a selected position. The operating table, support rail and collar mount 18 are in common usage and are of conventional design. Accordingly, they do not form a part of the present invention.

The limb restraint 10 is adapted to be supported from an aperture of the collar mount 18. Accordingly, the restraint 10 includes an upright leg 20 having parallel sides which are configured for reception in the matingly configured aperture of the collar mount 18. The leg 20 may be wider in an area above that which is adapted to be received in the collar mount 18. At the upper end of the leg 20, the frame 12 includes a horizontal section 22 which extends across the operating table at right angles to the leg 20. The leg 20 and the horizontal section 22 may be formed of one piece.

A unitary air bag support 24 is secured to the horizontal section 22. The air bag support 24 comprises a pair of spaced side panels 26, 28 joined by a top plate 30. The entire air bag support 24 may be suitably formed from a single piece of steel with the top plate 30 joined to the horizontal section 22 by conventional means such as a weld 32.

Figure 3:
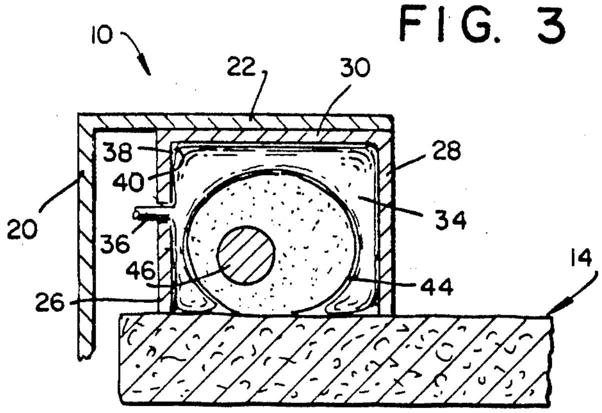
FIG. 3 is an enlarged scale fragmentary sectional view through the limb restraint as shown in FIG. 1, the same being taken substantially along the plane 3—3 of FIG. 1.

Pursuant to the present invention, the air bag support 24 carries an inflatable air bag cuff 34 (shown in FIGS. 1 and 3). A suitable air bag cuff which may be employed in conjunction with the present invention is a blood pressure or tourniquet cuff conventionally in use. Such air bags are available in various lengths and include a stem 36 to which standard tourniquet inflating equipment and regulator gauges for monitoring the pressure within the air bag are attached.

The air bag cuff 34 is fastened to the interior surfaces of the air bag support 24 with conventional hook and loop type strip fasteners 38, 40 such as those sold under the trademark Velcro. Accordingly, a strip 38 of either hook or loop material is secured to the interior surfaces of the air bag support 24 while a corresponding strip 40 of the mating material is secured to the periphery of the air bag cuff 34.

An aperture 42 is formed in the side panel 26; the air bag stem 36 projects through the aperture 42 for inflation of the bag and monitoring of the air pressure.

With reference now to FIGS. 1 and 3, the procedure employed for utilizing the limb restraint 10 in a typical arthroscopic knee joint examination will be described. The patient (shown in dashed lines in FIG. 1) is placed upon the operating table 14. Thereafter, the limb restraint is positioned above the patient with the side panels 26, 28 spanning the patient's thigh 44 and with the air bag cuff 34 deflated yet secured by the fasteners 38, 40 to the air bag support 24.

The frame 12 is then brought into engagement with the aperture in the slidable collar mount 18 and the restraint 10 lowered to the position shown in FIG. 3, that is enclosing the patient's thigh 44 with the ends of the side panels 26, 28 engaging a pad of the table 14. Thereafter, the limb is draped and a conventional tourniquet inflated to prevent the flow of blood during the arthroscopic examination.

The air bag cuff 34 is inflated through the stem 36 with conventional inflating equipment until the pressure applied to the thigh 44 is in the range of 150 to 250 millimeters of mercury. With such pressure applied to the thigh through the air bag 34, the patient's femur 46 is suitably restrained from movement without injury to thigh tissue and/or muscles.

Arthroscopic examination and/or surgery may thereafter be performed with the lower leg being manipulated in a lateral or medial direction to apply valgus or varus stress respectively to the knee joint. During application of such stress to the knee joint through manipulation of the free portion of the patient's limb, the air bag 34 provides even distribution of restraining force against the thigh 44.

Figure 4:
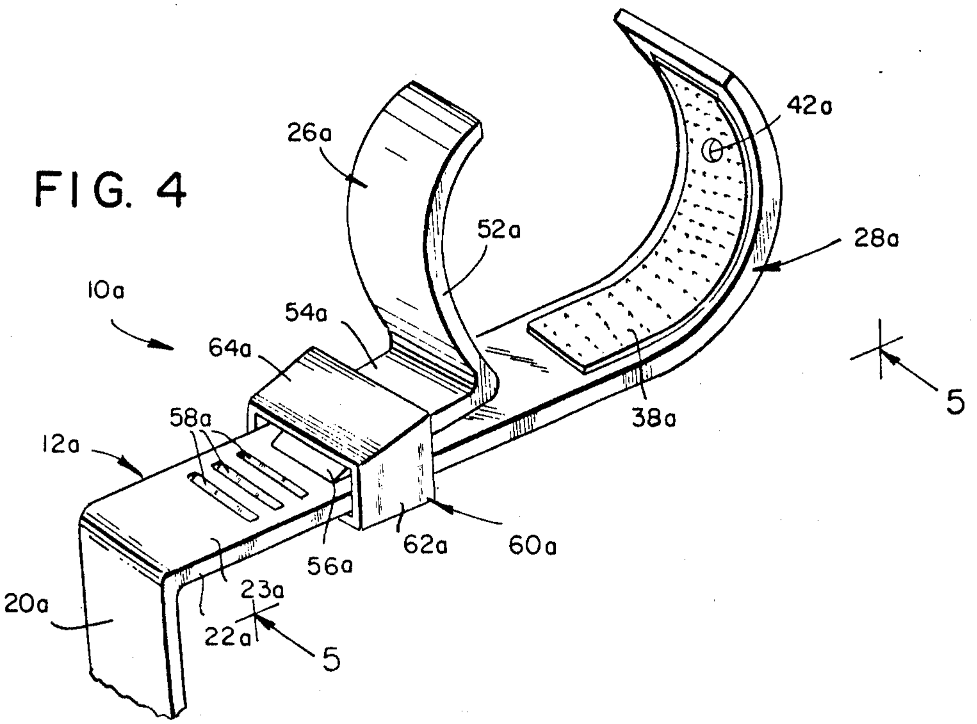
FIG. 4 is a fragmentary perspective illustration of a limb restraint frame constructed in accordance with an alternate embodiment of the invention with the air bag removed and illustrating an adjustably positioned jaw having a tang which engages one of a plurality of notches formed in a way.

An alternate embodiment of the invention is shown in FIGS. 4 through 6. In this embodiment, like numerals denote like components as disclosed with respect to the prior embodiment bearing the suffix "a", however.

A limb restraint **10*a* similar in construction to the limb restraint previously described includes a frame 12*a* which is secured to an operating table collar mount in a manner identical to that previously described with reference to the prior embodiment. Accordingly, the frame 12*a* includes an upright leg 20*a* similar in construction to the leg 20 previously described. At the upper end of the leg 20*a*, the frame 12*a* extends at a right angle to the leg 20*a*** and includes a horizontal section 22*a* which forms a way 23*a* along its upper surface. The section 22*a* extends transversely across the operating table in abutment against the mattress or pad of the table.

The section 22*a* terminates at an upwardly directed laterally curved jaw 28*a*. The concavity of curvature of the jaw 28*a* lies in a lateral direction.

A medially curved jaw 26*a* is adjustably secured to the section 22*a*. The jaw 26*a* includes an arcuate segment 52*a* which extends from a free upper end to a straight tang 54*a* which is formed at the lower end of the curvature. An acute angle is formed at the intersection of the tang 54*a* and the arcuate segment 52*a*. The tang 54*a* projects away from the convex surface of the jaw 26*a* and is of tapering thickness as the tang progresses from the arcuate segment 52*a*. The distal edge of the tang 54*a* includes a bevel 56*a*.

Adjustment of the position of the jaw 26*a* along the horizontal section 22*a* is provided by selecting the engagement between the free end of the bevel 56*a* with one of a plurality of notches 58*a* which extend transversely across the way 23*a*. Each notch 58*a* includes an abutment surface which is undercut, i.e. forms an acute angle with the plane of the way 23*a*. Inadvertent disengagement between the bevel 56*a* of the tang and the way is thus prevented.

A carriage 60*a* is employed to secure the jaw 26*a* at its selected position along the way. The carriage 60*a* includes a pair of opposed side walls 62*a* which engage the side edges of the horizontal segment 22*a*. The side walls 62*a* are joined by a top wall 64*a* with the carriage 60*a* retentively carried on the section 22*a* by inwardly bent portions of the side walls adjacent their lower ends which engage the undersurface of the section 22*a*.

It should be noted that the upper edge of the side walls 62*a* are sloped so that the top wall 64*a* lies at an acute angle with respect to the way 23*a*. Thus, when the jaws 26*a*, 28*a* are urged apart, the undersurface of the top wall 64*a* will urge the bevel 56*a* into more positive locking engagement with a selected notch 58*a*.

It should additionally be noted that, in a manner similar to that disclosed with reference to the prior embodiment, the inner surface of the fixed jaw 28*a* and a portion of the way 22*a* adjacent the jaw 28*a* includes a strip 38*a* of fastener material. In addition, a similar strip 38*a* is secured to the concave surface of the jaw 26*a*.

As with the prior embodiment, an air bag cuff 34*a* is positioned within and between the jaws 26*a* and 28*a*. The cuff 34*a* includes mating strips 40*a* of fastener material secured along its periphery. In addition, a trailing strip of fastener material 68*a* extends beyond one end of the air bag cuff 34*a* and a mating strip 70*a* is secured to the concave surface of the fixed jaw 28*a* adjacent its free end. As with the prior embodiment, an aperture 42*a* is formed in the fixed jaw 28*a* and an inflating stem 36*a* of the air bag 34*a* extends through the aperture.

In use, the limb restraint 10*a* is positioned on the operating table with the leg 20*a* in engagement with the collar mount of the operating table. It should be noted that, when initially placed in position, the movable jaw 26*a* is removed and the air bag cuff 34*a* secured to the concave surface of the jaw 28*a* and to a portion of the way 23*a* adjacent the jaw 28*a*. The patient is then placed on the operating table with the affected limb positioned against the portion of the air bag cuff 34*a* which is fastened to the frame. Thereafter, the air bag cuff 34*a* is wrapped about the patient's thigh, circumscribing the thigh and extending over the free end of the fixed jaw 28*a* as shown in FIG. 5. A strip 68*a* of fastener extends beyond the free end of the air bag cuff 34*a*. The air bag cuff 34*a* is secured in its wrapped position by joining the fastener strip 68*a* to a fastener strip 70*a* which has been secured to the convex periphery of the fixed jaw 28*a*.

The jaw 26*a* is then positioned in abutment against the exposed periphery of the air bag 34*a* and a suitable notch 58*a* in the way 23*a* is engaged by the edge of the bevel 56*a*. The carriage 60*a* is then slid from a position adjacent the leg 20*a* to the position shown in FIG. 5, wherein the undersurface of the top wall 64*a* engages the tang 54*a*. When jaw 26*a* is positioned, the fastener strip 38*a* secured to the concave surface of the movable jaw 26*a* will engage a mating fastener strip 40*a* secured to the periphery of the air bag 34*a*.

Thereafter, the air bag cuff 34*a* is inflated through the stem 36*a* in a manner identical to that described with reference to the previous embodiment. The force applied against the movable jaw 26*a* by the inflating air bag cuff 34*a* only serves to secure the engagement between the tang 54*a* and the selected notch 58*a* formed in the way 23*a*.

In FIG. 7, a further alternate embodiment of the invention is shown. In this embodiment, a limb restraint 10*b* similar to the limb restraint 10*a* is provided. The restraint 10*b* includes a frame 12*b* including a leg 20*b*, a horizontal section 22*b* and a fixed jaw 28*b*, all of which are similar in construction to the corresponding components of the limb restraint 10*a*. The horizontal segment 22*b* further includes a way 23*b* along its upper surface which, however, does not include notches.

A movable jaw 26*b* similar in construction to the jaw 26*a* is provided. The jaw 26*b* includes a tang 54*b* having a transverse aperture through which a pivot pin 72*b* is journalled. The pin 72*b* extends between a pair of bosses 74*b* which project from a top wall 64*b* of a carriage 60*b*. The carriage 60*b* is similar in construction to the carriage 60*a* previously described, however the top wall 64*b* is not angular and lies in a plane parallel to that of the way 23*b*. In addition, a thumb screw 76*b* threadingly engages an aperture formed in a side wall 62*b* and is adapted to engage a side edge of the horizontal section 22*b* to lock the carriage in position.

The fixed jaw 28*b* and a portion of the way 23*b* adjacent the jaw include a fastener strip 38*b* as does the convex surface of the movable jaw 26*b*. In addition, a further fastener strip 78*b* is adapted for placement across the free ends of the jaws 26*b*, 28*b* and engages mating fastener strips 80*b* secured to the convex surfaces of both jaws adjacent the ends.

In operation, the limb restraint 10*b* is initially set up in a manner quite similar to that described with reference to the limb restraint 10*a*. The carrier 60*b* is slid to a position adjacent the leg 20*b* and the movable jaw is pivoted away from the fixed jaw 28*b* to provide easy access for the patient's limb.

The patient's limb is placed against an air bag cuff which has been secured to the fastener strip 38*b*. The air bag cuff is thereafter wrapped about the patient's limb and the movable jaw 26*b* placed into position by sliding the carriage 60*b* toward the fixed jaw. The position of the carriage 60*b* is locked with the thumb screw 76*b* and the movable jaw 26*b* is pivoted toward the limb about the hinge pin 72*b*. The movable jaw is restrainted from pivoting away from the limb by placement of the fastener strip 78*b* across the free ends of both jaws.

The frames of the limb restraints herein described may be constructed of any suitable material such as steel stock or stainless steel. Additionally, radioparent materials such as aluminum alloys and reinforced plastics may be employed where desirable. It should also be appreciated that, although the leg which engages the collar mount has been illustrated as having a rectangular cross-sectional configuration, the shape of the leg is in fact a function of the particular fastening mechanism in the operating table collar mount.

Air bag cuffs or tourniquets suitable for use in conjunction with the limb restraint are readily available in various lengths from numerous surgical supply sources such as Zimmer located at Warsaw, Ind. The inflatable air bag employed in conjunction with the limb restraint provides for an even distribution of the restraintive forces. Additionally, since the air bag cuff inflates, it provides for automatic adjustment to fit various sized limbs.

While the limb restraint has been illustrated in an exemplary manner as suitable for knee joint arthroscopic examination and surgery, the present invention is employable for various operating procedures. For example, the limb restraint may be employed for restraining arms, ankles and other limb elements. In this regard, an air bag cuff of suitable length would, of course, be used. If necessary, smaller limbs and children's limbs could be restrained with smaller or adjustable frames in instances wherein the inflation limits of a given air bag cuff would not accommodate the limb.

Various changes to the limb restraint and method herein described are readily apparent to those skilled in the art. Accordingly, the present invention should not be constrained to the particular implementations herein described. For example, while the side walls of the air bag support have been shown as being planar and parallel to one another, such configuration is exemplary; alternate shapes are readily apparent. Similarly, although the alternate embodiments illustrate a single movable jaw and a single fixed jaw, both jaws could be provided either movable or fixed. In addition, while two possible mechanisms for adjustment of a movable jaw have been shown, other mounting and/or adjustment mechanisms should be readily apparent to those skilled in the art. Additionally, jaws need not be convexly curved toward one another and may be angularly bent along one or more transverse axes or extend parallel to one another in a manner similar to that of the side walls of the restraint of the first embodiment.

Thus, it will be seen that there is provided a limb restraint which achieves the various objects of the invention and which is well adapted to meet conditions of practical use.

As various changes might be made in the invention as above set forth, it is to be understood that all matter herein described or shown in the accompanying drawings is to be interpreted as illustrative and not in a limiting sense.

Having thus described the invention, there is claimed as new and desired to be secured by Letters Patent:

1. A limb restraining apparatus for use in combination with a table upon which a patient is resting, the patient having a limb to which a procedure comprising arthroscopic diagnosis and surgery is to be performed, the limb including an articulated joint, a proximal limb section disposed between the articulated joint and the patient's torso and a distal limb section extending from the articulated joint, the limb restraining apparatus being applied to the patient's limb about the proximal limb section, the limb restraining apparatus comprising peripherally confining means for restraining a zone of the proximal limb section substantially about a peripheral surface of the proximal limb portion except for an underside portion of the proximal limb section resting upon the table, the confining means including an open nonrestraining section in registry with the peripheral section of the patient's proximal limb section resting upon the table, the open nonrestraining section of the limb restraining apparatus comprising means for maintaining blood vessels within the limb in a zone registered with the restraining apparatus free of constrictions, the peripherally confining restraining means including means for restraining a b of the proximal limb section from movement while allowing movement and manipulation of the distal limb section, the peripherally confining means including a rigid support and a flexible support, the rigid support having frame means surrounding the top and sides of the limb section, means mounting the rigid support to the table, means mounting the flexible support within the rigid support, the flexible support bearing against the peripheral surface of the proximal limb section zone except for the underside portion of the proximal limb section resting upon the table.

2. A limb restraining apparatus constructed in accordance with claim 1 wherein the cuff is inflated to a pressure of between 150 and 250 millimeters of mercury.

3. A limb restraining apparatus for use in combination with a table upon which a patient is resting, the patient having a limb to which a procedure comprising, arthroscopic diagnosis and surgery is to be performed, the limb including an articulated joint, a proximal limb section disposed between the articulated joint and the patient's torso and a distal limb section extending from the articulated joint, the limb restraining apparatus being applied to the patient's limb about the proximal limb section, the limb restraining apparatus comprising peripherally confining means for restraining a zone of the proximal limb section substantially about a peripheral surface of the proximal limb section except for an underside portion of the proximal limb section resting upon the table, the confining means including an open nonrestraining section in registry with the peripheral portion of the patient's proximal limb section resting upon the table, the open nonrestraining section of the limb restraining apparatus comprising means for maintaining blood vessels within the limb substantially free of constrictions in a zone registered with the peripheral surface of the proximal limb section, the peripherally confining restraining means including means for restraining a bone of the proximal limb section from movement while allowing movement and manipulation of the distal limb section, the peripherally confining means including a rigid support and a flexible inflatable support, the rigid support having frame means surrounding the top and sides of the limb the flexible support bearing against the peripheral surface of the proximal limb section in the zone except for the underside resting upon the table, means mounting the rigid support to the table, means mounting the flexible support within the rigid support, the flexible support including an inflatable cuff, the means mounting the rigid support including means for adjustably positioning the peripherally confining means along the length of the table.

4. A limb restraining apparatus constructed in accordance with claim 3 wherein the cuff includes control and maintenance means for controlling and maintaining inflation pressure of the cuff at a substantially fixed value during the procedure.

5. A limb restraining apparatus constructed in accordance with claim 3 wherein the cuff contains gases at a pressure of between 150 and 250 millimeters of mercury.

6. A limb restraining apparatus constructed in accordance with claim 3 further including means for detachably mounting the cuff within the rigid support.

7. A limb restraining apparatus constructed in accordance with claim 3 wherein the cuff includes an inflation stem, the rigid support including an aperture, the stem extending through the aperture to facilitate inflation.

8. A method of accessing areas of a limb joint for insertion and manipulation of arthroscopic instruments during anthroscopic examination or surgery, the method comprising the steps of:

(a) confining a first zone of a limb with a frame surrounding the top and sides of the limb, said frame including on the inside an air bag cuff, the first zone being positioned between the patient's body and the joint;

(b) immobilizing the air bag cuff;

(c) inflating the cuff to a minimum predetermined pressure to restrain the first zone from movement;

(d) monitoring and maintaining the inflating pressure while stressing the limb joint, the stressing of the joint being attained by applying forces to a second zone of the limb, the second zone being spaced from the joint in a direction away from the patient's body.

9. A method of accessing areas of a limb joint in accordance with claim 8 wherein the limb is a leg, the joint comprising a knee joint, the first zone comprising a portion of a thigh, the step of immobilizing the air bag cuff comprising immobilizing the cuff adjacent the top and opposite sides of the thigh.

10. A method of accessing areas of a limb joint in accordance with claim 9 wherein the confining step includes positioning the cuff only around the top and sides of the thigh, the underside of the thigh being free of contact with the inflated cuff.

11. A method of accessing areas of a limb joint for insertion and manipulation of arthroscopic instruments in accordance with claim 9 wherein the joint is stressed by applying rotational stress to the second zone relative to the first zone.

12. A method of accessing areas of a limb joint in accordance with claim 8 wherein the step of immobilizing the cuff comprises fixing the cuff with respect to a rigid frame, the frame being operatively positioned to overlie the air bag cuff, the fixing step comprising peripherally securing the cuff to the frame, the frame being spaced from the first zone.

13. A method of restraining a portion of a limb of a patent resting upon a surgical table for orthopedic examination and operating procedures upon a joint of the limb, the method comprising the steps of:

(a) providing a restraining apparatus having rigid support means said support means having frame means surrounding the top and sides of the limb to be restrained and an inflatable cuff on the inside of the frame means;

(b) registering the restraining apparatus with a first zone of the limb, the first zone being spaced from the joint in a direction towards the patient's torso by adjustably anchoring the rigid support means to the table at a selected position along the length of the table, the support means being out of direct contact with the limb;

(c) peripherally confining the first zone of the limb except for an underside portion of the first zone resting upon the surgical table with the inflatable cuff;

(d) applying restraintive force to the first zone by inflating the cuff to a pressure of at least 150 millimeters of mercury while immobilizing portions of the cuff spaced from the first zone of the limb with the rigid support means;

(e) monitoring and maintaining the inflated pressure of the cuff for the duration of the operating procedure; and (f) separating portions of the joint to permit the insertion and manipulation of arthroscopic instruments by applying controlled forces to a second zone of the limb, the second zone being spaced from the joint in a direction away from the first zone.

14. A method of restraining a portion of a patient's limb during diagnostic or surgical procedures conducted upon a limb joint as set forth in claim 13 wherein the cuff includes an outer periphery, the step of inflating and immobilizing the cuff includes the step of anchoring the cuff to the rigid support means along the outer periphery of the cuff.

15. A method of restraining a portion of a patient's limb in conjunction with diagnostic or surgical procedures upon a limb joint as set forth in claim 14 wherein the rigid support means includes a frame having a depending leg, the step of anchoring including anchoring the support means to the table by inserting the leg into a collar mount which is slidable along the surgical table.

* * * * *